United States Patent [19]

Kincses et al.

[11] Patent Number: 5,061,729

[45] Date of Patent: Oct. 29, 1991

[54] PHARMACEUTICAL COMPOSITION AND PROCESS FOR PREPARING THE SAME

[75] Inventors: Gyula Kincses; Barna Kocsár; István Lampé; György Bacsa; László Krusper; István Kovács; Klára Barna née Katona; Ágnes Katona née Lendvay; Csongor Szabó; Zoltán Trestyánszky; István Télessy, all of Debrecen, Hungary

[73] Assignee: Biogal Gyogyszergyar, Debrecen, Hungary

[21] Appl. No.: 204,205

[22] Filed: Jun. 8, 1988

[51] Int. Cl.$^5$ .................. A01N 37/12; A01N 43/04
[52] U.S. Cl. ................... 514/562; 514/23; 514/24; 514/40; 562/554
[58] Field of Search .................. 514/23, 562

[56] References Cited

U.S. PATENT DOCUMENTS 3,091,569  5/1963  Sheffner .................. 514/562

FOREIGN PATENT DOCUMENTS

| 2305271 | 8/1973 | Fed. Rep. of Germany | 514/562 |
| 2470M | 4/1964 | France | 514/562 |
| 5691 | 2/1968 | France | 514/562 |
| 964989 | 7/1964 | United Kingdom | 514/562 |
| 1154914 | 6/1969 | United Kingdom | 514/562 |

OTHER PUBLICATIONS

Martindale, 28th Ed. (1982), pp. 49-50, and 644-645.
The Merck Manual, 14th Ed. (1982), pp. 1944-1955.
Tabachnik et al., "Studies on the Reduction of Sputum Viscosity in Cystic Fibrosis Using an Orally Absorbed Protected Thiol", J. Pharmacol. Exp. Ther. 214: 246-249, 1980.
Tobradex Package Insert, Alcon Labs.
Decadron Package Insert, Merck, Sharp and Dome.
Facts and Comparisons, Mar. 1988 update, pp. 493-497, 518-520a.
Rote Liste, 1979, pp. 177-178, No. 23, 177B, Editio Cantor, Aulendorf, Federal Republic of Germany, Fluimucil Antibiotic (The whole abstract).
Nebramycin, A New Broad Spectrum Antibiotic Complex, Wick, W. E. et al., Antimicrobial Agents and Chemotherapy, pp. 341-348 (1968).
Handbook of Common Drugs, pp. 7510, 7556 (Chinese).
The In Vitro Reduction of Viscosity of Human Tracheobronchial Secretions by Acetylcysteine, A. L. Sheffner et al., Am. Rev. Respir. Dis. 90, pp. 721-729 (1964).
Merck Index, 10th Edition, Compound 82.
Safety and Drug Interactions of Oral Acetylcysteine Related to Utilization Data, V. Ferrari, Eur. J. Respir. Dis. 1980, vol. 61, Suppl., pp. 151-157.
Effect of N-Acetylcysteine on Antibiotic Activity and Bacterial Growth in Vitro, Michael F. Parry et al., J. Clinical Microbiol., vol. 5, No. 1, pp. 58-61 (Jan. 1977).

Primary Examiner—Jerome D. Goldberg
Assistant Examiner—T. J. Criares
Attorney, Agent, or Firm—Herbert Dubno; Jonathan Myers

[57] ABSTRACT

The invention relates to pharmaceutical compositions as well as the preparation thereof which are useful for improving the status of patients suffering from external otitis or otitis (otitis media), or particularly from a chronic otitis (otitis media chronica). The pharmaceutical compositions according to the invention contain a sulfhydryl-containing compound, an antibacterial chemotherapeutic agent, an aspecific antiinflammatory agent and optionally a kerotolytic agent. The compositions preferably contain N-acetyl-L-cysteine as sulfhydryl-containing compound.

6 Claims, No Drawings

PHARMACEUTICAL COMPOSITION AND PROCESS FOR PREPARING THE SAME

This invention relates to novel pharmaceutical compositions useful for improving the status of patients suffering from external otitis or otitis (otitis media), particularly from a chronic otitis (otitis media chronica) as well as for restoring the healthy conditions of the middle ear.

According to an other aspect of the invention, there is provided a process for the preparation of the novel compositions.

Chronic otitis is a diasease occurring in both adult age and childhood which affects a relatively high percentage of the population. Not only the acute complications but also the bradyacusia (hardness of hearing) and surdity emerging later on can be avoided by an early diagnosis and suitable therapy. The deterioration of hearing of about one fourth of all the patients suffering from hardness of hearing can be attributed to inflammations endured in childhood and developing frequently in connection with infective diseases. Both the subacute and chronic otitis are found in a higher percentage of children who frequently suffered from otitis. Essential characteristics of this desease are a discontinuity of the eardrum, alterations of the tympanic cavity and recurrent recrudescences of the symptoms. In addition to the common reacions following the imflammation, the local symptoms may be manifest or latent. In the absence of therapy, these processes may lead to life-threatening complications.

In mesotympanic chronic otitis, the large central eardrum perforation, abundant mucous discharge and mucosa proliferation are characteristic. Bone damage or chronic mastoiditis may easily develop. The microorganisms, which are easily cultured from the discharge, belong to Staphylococcus and Pseudomonas genera.

A less and marginal perforation as well as eardrum epithelial metaplasia and a lower extent of discharge are characteristic of the epitympanic chronic otitis: the discharge is very thick, frequently purulent and stinking. The keratinizing flat epithelium of the auditory meatus penetrates into the tympanic cavity, replaces the mucous membrane taking place there under normal conditions and, due to the continuous detachments, forms there an epithelial cell mass, the so-called cholesteatoma. This thick mass spoils the bone formations of the tympanic cavity and finally, it may induce life-threatening complications. The inflammation occurring in such cases is not only a process of the mucous membrane but also extends to the bone. The superinfection is also characteristic of this form of chronic otitis.

Thus, the characteristic feature of chronic otitis in these cases consists therein that, due to the discontinuity of the eardrum, the tympanic cavity has a free contact with the outside world and, with the advance of the pathologic processes irreversible damage of the eardrum takes place and thereby, considerable auditory defect is induced which increases proportionately with the duration of the disease. In addition, the eardrum may completely be destroyed as a consequence of the inflammatory processes.

Earlier ear drops containing boric acid, alcohol, hydrogen peroxide, silver nitrate, trichloroacetic acid, ultraseptyl, balsamics or chloramphenicol were suggested for the therapy of such diseases. These ear drops were useful for the symptomatic treatment and for relieving the symptoms of the secondary superinfection, however, they were not capable to promote the removal of the discharge or the cholesteatoma and to prevent simultaneously the bacterial and fungal infections. Further on, no commonly available composition is known at present which is suitable to alter the consistency of the ear discharge and thus to promote the easier leaving or the removal of the discharge from the ear. There are frequently described otologic compositions which cannot be used for an open tympanic cavity.

There are generally known combinations preferably containing an aminoglycoside antibiotic together with an aspecific antiimflammatory agent. In spite of a possible synergistic effect, such combinations are not capable to cure the complex ear diseases though, in certain cases they can prevent the further propagation of the bacterial infection and the chronic development of inflammations; however, due to their composition, they are unable to promote also the simultaneous leaving of the discharges in addition to the above-mentioned treatment of the ear discharge. Namely, when investigating the etiology of otitis, this is indispensable.

Based on this knowledge, the object of the present invention is to provide compositions which exert an adequate mucolytic and/or keratolytic effect in the case of a perforated eardrum and are capable to suppress the destructive effects of bacteria and fungi.

The invention is based on the surprising recognition that, due to their mucolytic and keratolytic effects, compounds containing sulfhydryl group(s) together with other commonly known drugs can successfully be used for treating patients suffering from chronic otitis (otitis media chronica).

More specifically, the invention relates to an ear drop composition for the treatment of chronic otitis media, which consists essentially of:

(a) 3 to 19% by weight of a sulfhydryl compound selected from the group consisting of N-acetyl-L-cysteine, disulfiram, and pantetheine or a pharmaceutically acceptable salt thereof effective to reduce viscosity of a viscous, superinfected, protein-containing discharge trapped within the middle ear of a mammalian subject suffering from chronic otitis media;

(b) a therapeutically effective amount of an antibacterial agent selected from the group consisting of tobramycin, neomycin, polymixin B, gentamycin, a combination of tobramycin and neomycin in a 1:1 weight ratio, and a combination of polymixin B and neomycin, tobramycin, or gentamycin in a ratio of 100,000 IU to about 100 mg, or a pharmaceutically acceptable salt thereof;

(c) a therapeutically effective amount of an anti-inflammatory agent selected from the group consisting of hydrocortisone, mazipredone, beclomethasone dipropionate, triamcinolone acetonide, prednisolone, dexamethasone, and betamethasone, or a pharmaceutically acceptable salt thereof; and (d) the balance an aqueous solution of propylene glycol; in admixture with zinc oxide in an amount effective to stabilize the sulfhydryl compound.

The mucolytic action of a group of sulfhydryl-containing compounds for treating respiratory diseases has been described in several forms. A number of pharmaceutical compositions containing such active ingredients such as Mucomyst, Mucolyticum Lappe, Fluimucil, Aibron, Acetein and Mucosolvin are commercially available.

The utility of sulfhydryl-containing compounds for reducing the mucous viscosity was proved in a number of cases both by local and oral or parenteral treatments as well. One of the most commonly used sulfhydryl-containing compounds is acetylcysteine satisfying the requirements of an oral administration on the basis of its $LD_{50}$ values:

$LD_{50}$ in dogs = 1000 mg/kg of body-weight;
$LD_{50}$ in rats = 6000 mg/kg of body-weight; and
$LD_{50}$ in mice = 3000 mg/kg of body-weight.

In the respiratory diseases the implantation of bacterial flora becomes more difficult simultaneously with the decrease of the mucous viscosity. According to an other important observation, the bacteria are neither encapsulated nor morphologically altered in the presence of sulfhydryl-containing compounds.

This observation can be explained by the mode of action of the sulfhydryl-containing compounds, more particularly by the exchange reactions resulting in the separation of peptide chains.

The invention is based on the observation that, similarly to the respiratory diseases, a highly viscous superinfected discharge of a high protein content is formed in most patients suffering from otitis (otitis media) which discharge is frequently unable to flow out even through the perforated eardrum. During our inventigations, it has surprisingly been found that, in a suitable environment, compounds containing sulfhydryl group(s) are capable in vitro to reduce the viscosity of these types of discharges rapidly and significantly. In the presence of sulfhydryl-containing compounds, e.g. several acylcysteines at a pH value of 6.7 to 7.5, the ear discharges taken from the patients become in vitro liquid within a short time.

In our further investigations involving cases with inflammation and superinfection, sulfhydryl compounds of different structure were combined with antibacterial, aspecific antiinflammatory and optionally keratolytic drugs. In accord with the observation of the prior art, it has been found that, in the cases of several combinations, the compounds containing reactive sulfhydryl groups are capable to take part in an undesired reaction with some aldehydes, epoxides lactones and $\beta$-lactams [Eur. J. Respir. Dis. 61, Suppl. 11, pp. 151-157 (1980)]. However, the absorption of several antibiotics from the stomach is not disadvantageously influenced by the sulfhydryl-containing compounds, particularly by acetylcysteine. Such antibiotics include inter alia amoxicillin, tobramycin, doxycyclin, neomycin and erythromycin. A certain but not significant extent of retardation may be observed with cephalexin; however, by assuring a relatively acidic pH value, this extent can be reduced. Based on these findings, it seemed possible to provide conditions, where the sulfhydryl-containing compounds are present in a stable composition together with the antibiotic types mentioned above.

According to the observation of M. F. Parry et al. [J. Clin. Microbiol. 5, pp. 58-61 (1977)], compounds containing a sulfhydryl group, particularly the acylcysteines are capable to inhibit the growth of several gram-positive and gram-negative bacteria such as *Pseudomonas aeruginosa*. Under the experimental conditions used, acetylcysteine shows a synergistic effect with several antibiotics under in vitro conditions.

Further on, our investigations led to the result that, out of the compounds containing a sulfhydryl group, N-acetyl-L-cysteines and their pharmaceutically acceptable salts such as the sodium or ammonium salt or the zinc mercaptide salt give the best results; however, a mucolytic effect can also be shown by using other compounds such as dithioerythritol, disulfiram, dimercaptosuccinate, glutathione, pantetheine or carbocysteine.

Within our investigations, acetylcysteine, particularly N-acetyl-L-cysteine proved to be the most useful mucolytic agent showing a pH value between 2.0 and 2.76 in an aqueous solution of 1% concentration. The N-acetyl-L-cysteine shows the highest viscosity-reducing action at a pH between 6.0 and 8.0. When this agent is used in the form of its pharmaceutically acceptable salts, the pH-dependance is not so much significant, however, the mucolytic activity of the salts is lower than that of the N-acetyl-L-cysteine [Am. Rev. Respir. Dis. 90, pp. 721-729 (1964)].

For combatting the bacterial infection occurring in the inflammation antibacterial chemotherapeutics, commonly employed in the dermatological therapy may be used. Such drugs are e.g. neomycin, polymyxin B, gentamycin, tobramycin, paromomycin, tetracyclins, chloramphenicol, nitrofurazone derivatives, tyrothricine, fusidic acid, amphomycin, the penicillins and cephalosporins as well as the therapeutically acceptable derivatives of these compounds.

In the compositions according to the invention steroids, synthetic corticoids such as hydrocortisone, dexamethasone, fluocinolone, fludroxycorticoid, cortisone acetate, triamcinolone acetonide, fluocinolone acetonide, mazipredone hydrochloride and beclomethasone dipropionate are preferably used as antiinflammatory agents.

The compositions according to the invention may optionally contain also desquamatory agents such as tretinoin, salicylic acid or its derivatives as well as benzoic acid and resorcinol. The compounds investigated are usually capable to remove effectively the flat epithelium penetrating into the tympanic cavity or the cholesteatoma.

The most preferred formulation of the mucolytic and chemotherapeutic compositions according to the invention is the ear drop namely, the drops, having a liquid consistency penetrate easily to the sites of the accumulated thick and viscous discharge and promote its relatively easy removal.

In the course of therapeutically investigating the ear drops of the above composition, the following observations have been made.

In the case of external diffuse eczematous otitis (otitis externa diffusa ekzematosa) the effect was very favorable: an improvement or restoration was observed in about 86% of the patients. Furthermore, a great part of the improved cases could be completely cured by a drying post-treatment.

In the cases of chronic cholesteatomatous otitis (otitis media chronica cholesteatomatosa), it could be observed that the cholesteatomatous mass was more easily removable by an otologic aspirating equipment than in the cases without the treatment.

During the therapeutical study of the composition according to the invention, the advance of the pathological process was not observed in any case; no side-effect appeared which could motivate to cease the treatment.

By using the compositions according to the invention, the period of the restoration was reduced thus, the pathological state was much earlier improved. It is thought to be most important that after the use of the composition according to the invention the amount of the ear discharge was suddenly reduced and its consistency was also significantly modified. The ear discharge did not become in general a more thin-liquid but its viscosity was diminished by obtaining a precipitate-like character. No increase in the amount of discharge was observed.

Several compositions according to the invention were also studied with omitting one active ingredient of the composition in order to support the progressive character of the multi-active-component type composition according to the invention. These experiments led to the following results.

The use of an 1% to tobramycin solution resulted in a substantial improvement of the pathological processes in about 60% of patients suffering from chronic mesotympanic otitis; this ratio did not exceed the 40% in the patients suffering from external otitis.

When administering only a steroid, the greater part of the patients were subjectively improved however, the objective signs of the improvement were not convincing. An objective improvement was observed only in those cases involving large eardrum defects, strong hyperaemia and significant mucous membrane hypertrophy of the tympanic cavity as well as in the cases of external eczematous otitis (otitis externa ekzematosa).

Surprisingly, aqueous solutions (pH 7.0±0.2) of 3 to 19%, preferably 5 to 15% of compounds containing the sulfhydryl group such as acylcysteines, preferably N-acetyl-L-cysteine advantageously influenced the viscosity of the discharge and simultaneously moderated the inflammatory symptoms, too. The dilution of the discharge was not observed during the use, however, the amount of the discharge was somewhat reduced in spite of the decrease of its viscosity. The discharge, which was coherent and mucous in character, rather took the form of a precipitate under effect of the treatment by an acetylcysteine solution.

In the Department for Otorhinolaryngology of the Medical University of Debrecen, adult and child patients were examined to identify the types of pathogenic micro-organisms occurring in the discharges of patients suffering from chronic otitis (otitis media chronica); the discharges of 510 patients were analyzed for the bacterial infection. The results obtained by the analysis of the ear discharge of 279 children and 231 adults are summarized in Table 1.

TABLE 1

The frequency of pathogenic microorganisms

| Pathogen | Number of cases | % of cases |
|---|---|---|
| Staphylococcus aureus | 164 | 32.15 |
| Pseudomonas aeruginosa | 78 | 15.29 |
| Staphylococcus epidermidis | 71 | 13.92 |
| Pseudomonas sp. | 39 | 7.64 |
| Proteus sp. | 32 | 6.27 |
| Escherichia coli | 31 | 6.07 |
| Klebsiella sp. | 23 | 4.5 |
| Streptococcus alpha-haemolyticus | 14 | 2.74 |
| Bacillus sp. | 13 | 2.54 |
| Streptococcus faecalis | 11 | 2.15 |
| Streptococcus beta-haemolyticus | 10 | 1.96 |
| Escherichia alkal. dispar | 8 | 1.56 |
| Streptococcus pneumoniae | 7 | 1.37 |
| Haemophylus sp. | 5 | 0.98 |
| Acinetobacter sp. | 3 | 0.58 |
| Alcaligenes faecalis | 1 | 0.19 |
|  | 510 | 100.00 |

It was concluded from the observations that an important identity of the bacterial infection exists in the otitis cases of adult and child patients. As it can clearly be seen from Table 1, the most frequently occurring pathogens are Staphylococcus aureus, Pseudomonas aeruginosa and Staphylococcus epidermidis.

Hereinafter, the results of the treatment of the discharges by antibacterial agents are summarized in Table 2.

TABLE 2

| Active ingredient | 0 | R | M | A | Act. |
|---|---|---|---|---|---|
| Neomycin | 465 | 5 | 13 | 27 | 88.9 |
| Tobramycin | 247 | 61 | 86 | 116 | 79.2 |
| Oxacillin | 229 | 77 | 13 | 191 | 72.6 |
| Meticillin | 242 | 95 | 27 | 146 | 64.6 |
| Carbenicillin | 260 | 91 | 22 | 137 | 63.6 |
| Gentamycin | 255 | 118 | 72 | 65 | 53.7 |
| Cephaloridin | 131 | 182 | 27 | 170 | 51.9 |
| Streptomycin | 342 | 87 | 42 | 39 | 48.2 |
| Polymyxin B | 330 | 103 | 8 | 69 | 42.7 |
| Ampicillin | 307 | 120 | 11 | 72 | 40.8 |
| Oleandomycin | 213 | 179 | 4 | 114 | 39.7 |
| Chloramphenicol | 196 | 197 | 11 | 106 | 37.2 |
| Co-trimoxazole | 99 | 259 | 12 | 140 | 36.9 |
| Erythromycin | 183 | 208 | 6 | 113 | 36.4 |
| Penicillin | 203 | 218 | 22 | 67 | 29.4 |
| Tetracyclin | 136 | 279 | 16 | 79 | 25.4 |
| Total number of the examinations: 510 | | | | | |

Symbols used in Table 2:
0 = number of the cases not examined
R = inactive (resistant)
M = moderately active
A = therapeutically active (sensitive)
Act. = activity %

In the course of investigation of the fungi species occurring in the ear discharges it was determined that, in accord to the literature, the most characteristic species in this disease are *Aspergillus flavus*, *Aspergillus fumigatus*, *Aspergillus niger* and *Candida albicans*.

The ear drop compositions according to the invention are prepared as described hereinafter.

About one half of the required amount of propylene glycol is added to the most part of the required amount of water then, with keeping of the following order of addition, the sulfhydryl-containing compound is first added, which compound is preferably completely soluble in the medium or suitable to form a microcrystalline suspension. After an eventual clearing of the solution zinc oxide is added which may be dissolved even in one hour even while stirring. Zinc oxide is used for stabilizing the sulfhydryl compounds.

Subsequently, the pH value of the solution or suspension is modified by adding preferably sodium hydroxide, then the antibacterial ingredient suitably chosen from the group of the aminoglycosides is introduced. After adding the second half of propylene glycol, the antiinflammatory ingredient is added, while taking care to maintain the pH value at 7.0±0.1 by portion-wise addition of 1M sodium hydroxide solution. On introducing the antiinflammatory agent the complete dissolution is not required in each case; optionally a microcrystalline suspension is prepared.

After introducing the antiinflammatory ingredient the other auxiliary and additive materials are added, then if necessary the solution is filtered and formulated in each case in a sterile form.

The compositions and process according to the invention are illustrated in detail in the following non-limiting Examples.

EXAMPLE 1

Preparation of a Microcrystalline Suspension

Components:

| | |
|---|---|
| N-Acetyl-L-cysteine | 500 mg |
| Tobramycin sulfate | 100 mg |
| Hydrocortisone acetate (microcrystalline) | 100 mg |
| Neomycin sulfate | 100 mg |
| Aqueous solution of propylene glycol up to | 10.0 ml |

EXAMPLE 2

Preparation of a Solution

Components:

| | |
|---|---|
| N-Acetyl-L-cysteine | 500 mg |
| Tobramycin sulfate | 100 mg |
| Mazipredone hydrochloride | 50 mg |
| Neomycin sulfate | 100 mg |
| Aqueous solution of propylene glycol up to | 10.0 ml |

EXAMPLE 3

Components:

| | |
|---|---|
| N-Acetyl-L-cysteine | 500 mg |
| Polymyxin B sulfate | 100,000 IU |
| Neomycin sulfate | 100 mg |
| Mazipredone hydrochloride | 50 mg |
| Aqueous solution of propylene glycol up to | 10.0 ml |

EXAMPLE 4

Components:

| | |
|---|---|
| Disulfiram | 500 mg |
| Salicylic acid | 500 mg |
| Polymyxin B sulfate | 100,000 IU |
| Neomycin sulfate | 100 mg |
| Hydrocortisone acetate | 100 mg |
| Aqueous solution of propylene glycol up to | 10.0 ml |

EXAMPLE 5

Components:

| | |
|---|---|
| Pantetheine | 450 mg |
| Benzoic acid | 100 mg |
| Polymyxin B sulfate | 100,000 IU |
| Neomycin sulfate | 100 mg |
| Beclomethasone dipropionate | 100 mg |
| Aqueous solution of propylene glycol up to | 10.0 ml |

EXAMPLE 6

Components:

| | |
|---|---|
| N-Acetyl-L-cysteine | 850 mg |
| Tobramycine sulfate | 100 mg |
| Hydrocortisone acetate (microcrystalline) | 100 mg |
| Aqueous solution of propylene glycol up to | 10.0 ml |

EXAMPLE 7

Components:

| | |
|---|---|
| N-Acetyl-L-cysteine | 1100 mg |
| Neomycin sulfate | 100 mg |
| Mazipredone hydrochloride | 60 mg |
| Aqueous solution of propylene glycol up to | 10.0 ml |

EXAMPLE 8

Components:

| | |
|---|---|
| N-Acetyl-L-cysteine | 600 mg |
| Tobramycin sulfate | 100 mg |
| Triamcinolone acetonide | 40 mg |
| Benzoic acid | 120 mg |
| Aqueous solution of propylene glycol up to | 10.0 ml |

EXAMPLE 9

Components:

| | |
|---|---|
| N-Acetyl-L-cysteine | 500 mg |
| Tobramycin sulfate | 125 mg |
| Hydrocortisone acetate (microcrystalline) | 100 mg |
| Aqueous solution of propylene glycol up to | 10.0 ml |

EXAMPLE 10

Components:

| | |
|---|---|
| N-Acetyl-L-cysteine | 600 mg |
| Tobramycin sulfate | 125 mg |
| Mazipredone hydrochloride | 50 mg |
| Aqueous solution of propylene glycol up to | 10.0 ml |

EXAMPLE 11

Components:

| | |
|---|---|
| N-Acetyl-L-cysteine | 550 mg |
| Tobramycin sulfate | 125 mg |
| Dexamethasone sodium phosphate | 10 mg |
| Aqueous solution of propylene glycol up to | 10.0 ml |

EXAMPLE 12

Components:

| | |
|---|---|
| N-Acetyl-L-cysteine | 700 mg |
| Polymyxin B sulfate | 100,000 IU |
| Tobramycin sulfate | 125 mg |
| Prednisolone sodium succinate | 50 mg |
| Aqueous solution of propylene glycol up to | 10.0 ml |

EXAMPLE 13

Components:

| | |
|---|---|
| Disulfiram | 500 mg |
| Salicylic acid | 500 mg |
| Polymyxin B sulfate | 100,000 IU |
| Gentamycin sulfate | 100 mg |
| Dexamethasone sodium phosphate | 10 mg |
| Aqueous solution of propylene glycol up to | 10.0 ml |

EXAMPLE 14

Components:

| | |
|---|---|
| Pantetheine | 450 mg |
| Benzoic acid | 100 mg |
| Polymyxin B sulfate | 100,000 IU |
| Tobramycin sulfate | 100 mg |
| Betamethasone disodium phosphate | 10 mg |
| Aqueous solution of propylene glycol up to | 10.0 ml |

What is claimed is:

1. An ear drop composition for the treatment of chronic otitis media, which consists essentially of:
   (a) 3 to 19% by weight of a sulfhydryl compound selected from the group consisting of N-acetyl-L-cysteine, disulfiram, and pantetheine or a pharmaceutically acceptable salt thereof effective to reduce viscosity of a viscous, superinfected, protein-containing discharge trapped within the middle ear of a mammalian subject suffering from chronic otitis media;
   (b) a therapeutically effective amount of an antibacterial agent selected from the group consisting of tobramycin, neomycin, polymixin B, gentamycin, a combination of tobramycin and neomycin in a 1:1 weight ratio, and a combination of polymixin B and neomycin, tobramycin, or gentamycin in a ratio of 100,000 IU to about 100 mg, or a pharmaceutically acceptable salt thereof;
   (c) a therapeutically effective amount of an anti-inflammatory agent selected from the group consisting of hydrocortisone, mazipredone, beclomethasone dipropionate, triamcinolone acetonide, prednisolone, dexamethasone, and betamethasone, or a pharmaceutically acceptable salt thereof; and
   (d) the balance an aqueous solution of propylene glycol; in admixture with zinc oxide in an amount effective to stabilize the sulfhydryl compound.

2. The ear drop composition defined in claim 1 wherein the sulfhydryl compound is N-acetyl-L-cysteine or a pharmaceutically acceptable salt thereof.

3. The ear drop composition defined in claim 1 wherein the antibacterial agent is tobramycin sulfate.

4. The ear drop composition defined in claim 1 wherein the sulfhydryl compound is N-acetyl-L-cysteine or a pharmaceutically acceptable salt thereof, the antibacterial agent is tobramycin sulfate and the anti-inflammatory agent is dexamethasone sodium phosphate.

5. A method of treating chronic otitis media which comprises the step of administering to the ear of a mammalian subject in need of said treatment a therapeutically effective amount of the ear drop composition defined in claim 1.

6. A method of treating chronic otitis media which comprises the step of administering to the ear of a mammalian subject in need of said treatment a therapeutically effective amount of the ear drop composition defined in claim 4.

* * * * *